(12) United States Patent
Terasaki et al.

(10) Patent No.: US 6,346,259 B1
(45) Date of Patent: Feb. 12, 2002

(54) METHOD FOR PREPARING OF BETAINE ALKYL ESTER MIXTURE

(75) Inventors: Hiroyuki Terasaki; Akira Fujiu, both of Wakayama; Kazuhisa Fukuhara; Yoshihisa Kitano, both of Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/458,992

(22) Filed: Dec. 10, 1999

(30) Foreign Application Priority Data

Dec. 28, 1998 (JP) .................................. 10-373043

(51) Int. Cl.$^7$ .................................. A61K 7/06
(52) U.S. Cl. .................................. 424/401
(58) Field of Search .................................. 424/407

(56) References Cited

U.S. PATENT DOCUMENTS

| | | | | |
|---|---|---|---|---|
| 5,798,095 A | * | 8/1998 | Racky | 424/70.19 |
| 5,961,999 A | * | 8/1998 | Bimczok et al. | 424/401 |

FOREIGN PATENT DOCUMENTS

| | | |
|---|---|---|
| DE | 3527974 | 2/1987 |
| DE | 19520859 | * 12/1996 |
| JP | 49-76818 | 7/1974 |
| JP | 58-157750 | 9/1983 |
| JP | 09295960 | * 11/1997 |

OTHER PUBLICATIONS

Patent Abstracts of Japan, vol. 007, No. 277 (C–199), Dec. 9, 1983, JP 58–157750, Sep. 19, 1983.

* cited by examiner

*Primary Examiner*—Barbara P. Badio
(74) *Attorney, Agent, or Firm*—Oblon, Spivak, McClelland, Maier & Neustadt, P.C.

(57) ABSTRACT

The present invention provides a method for the easy preparation of a mixture comprising betaine alkyl ester which gives good softness, smoothness and oily feeling to hair. Thus, according to the present invention, a specific monohalogen carboxylic acid alkyl-ester is made to react with a specific tertiary amine using a specific long-chain alcohol as a reaction solvent and, after a specific betaine alkyl ester is obtained, the excessive above-mentioned tertiary amine is removed whereupon a mixture comprising the said long-chain alcohol and the said betaine alkyl ester is obtained.

1 Claim, No Drawings

METHOD FOR PREPARING OF BETAINE ALKYL ESTER MIXTURE

TECHNICAL FIELD

The present invention relates to a betaine alkyl ester mixture, to a method for preparing the same and to a cosmetic for hair comprising the said mixture.

BACKGROUND ART

In giving good softness, smoothness and oily feeling to hair, an agent-form in which a surfactant is emulsified in a gelatinous state using a long-chain alcohol such as cetanol is used. With regard to the surfactant, cationic surfactants are suitable and, among them, betaine alkyl ester is a surfactant which is able to give softness, smoothness and oily feeling particularly in a wet state. Incidentally, the betaine alkyl ester may be glycine betaine alkyl ester.

With regard to a method for the preparation of the betaine alkyl ester, JP-A 49-76818 reports a preparing method where betaine is made to react with alcohol using a dehydrating solvent such as toluene and an acidic catalyst of a sulfonic acid type and JP-A 58-157750 reports a preparing method where monochloroacetate is made to react with trimethylamine in a dialkyl ketone solvent. However, in these methods, it is necessary to remove the solvent and, therefore, there is a disadvantage that the process for the preparation is long. There is a problem in safety unless the solvent is completely removed.

Incidentally, when a quaternizing reaction is carried out by the reaction of a halogen compound with an amine compound and then a product is used without removing the solvent from the reaction final product, water or ethanol is used as a solvent. However, when such a solvent is used, hydrolysis, transesterification with ethanol, etc. take place and, if the reaction final product is used as it is, there is a disadvantage that a long-chain alcohol cannot be emulsified into gelatinous state and that softness, smoothness and oily feeling to hair is not obtained.

DISCLOSURE OF THE INVENTION

An object of the present invention is to provide a method for the preparation of a betaine alkyl ester mixture which is able to emulsify a long-chain alcohol even when the reaction final product is used and is able to give sufficient softness, smoothness and oily feeling to hair.

The present invention provides a method for preparing a betaine alkyl ester mixture, which comprises reacting a monohalogen-carboxylic acid alkyl-ester represented by the following formula (1):

$$R^1\text{—O—CO—}R^2\text{-X} \tag{1}$$

wherein $R^1$ is a linear or branched alkyl group or alkenyl group having 8–40 carbon atoms; $R^2$ is a linear or branched alkylene group having 1–5 carbon atoms; and X is a halogen atom;

with a tertiary amine represented by the following formula (2):

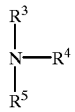

(2)

wherein $R^3$, $R^4$ and $R^5$ are same as or different from each other and each of them is a linear or branched alkyl group, alkenyl group or hydroxyalkyl group having 1–24 carbon atoms, using a long-chain alcohol represented by following formula (3) as a reaction solvent:

$$R\text{—OH} \tag{3}$$

wherein R is a linear or branched alkyl group or alkenyl group having 8–40 carbon atoms on average;

to prepare the betaine alkyl ester mixture comprising a betaine alkyl ester represented by the following formula (4):

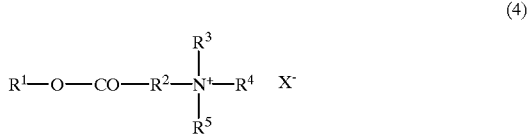

(4)

wherein $R^1$, $R^2$, $R^3$, $R^4$, $R^5$ and X have the same meanings as defined above, and the long-chain alcohol represented by the above-mentioned formula (3).

The present invention also provides a betaine alkyl ester mixture obtained by the above-mentioned method and a cosmetic for hair containing the said mixture. The present invention further offers an emulsion of the mixture. Furthermore, the present invention is a use of the betaine alkyl ester mixture as a cosmetic for hair. Still further, the present invention is a method for the treatment and make-up of hair with the betaine alkyl ester mixture.

Incidentally, the betaine alkyl ester of the present invention may be glycine betaine alkyl ester.

The betaine alkyl ester mixture obtained by the preparing method of the present invention can be used without removal of the long-chain alcohol used as a solvent and preparation thereof is possible by a simple preparing flow where the yield does not lower and neither removal nor recovery of the solvent is necessary. Moreover, the cosmetic for hair comprising the mixture prepared by the preparing method of the present invention has a good emulsifying ability for a long-chain alcohol and the like and is able to give good softness, smoothness and oily feeling to hair.

In the preparing method of the present invention, a step of separating the used solvent can be omitted. In addition, betaine ester can be obtained in a high yield.

MODES FOR CARRYING OUT THE INVENTION

In the formula (1) for the compound (1), $R^1$ is preferably a linear or branched alkyl group or alkenyl group having 10–36 carbons and particularly preferably 12–22 carbons, and $R^2$ is preferably selected from a methylene group, an ethylene group and an n-propylene group. With regard to X, a chlorine atom is particularly preferred. The compound (1) is a product of esterification of alcohol with a monohalogen-carboxylic acid or its lower alcohol ester, acidchloride, acid anhydride, etc. Thereof and its examples are cetyl monochloroacetate, stearyl monochloroacetate, tetradecyl monobromoacetate and cetyl monochloropropionate. Cetyl monochloroacetate is preferred.

In the formula (2) for the compound (2), each of $R^3$, $R^4$ and $R^5$ is preferred as methyl, ethyl, hydroxyethyl and hydroxypropyl groups. Example of the compound (2) includes trimethylamine, triethylamine, dimethylethylamine, dimethylethanolamine, dimethylpropanolamine and triethanolamine. Trimethylamine and dimethylethylamine are preferred.

In the formula (3) for the compound (3) used as a solvent, the number of carbon atoms in R is 8–40, preferably 12–20, and particularly preferably 14–18. When the number of carbon atoms in R is 8 or more, smell and emulsification of the product are good, and when the number of carbon atoms is 40 or less, melting point of the product is low whereby its handling is easy. Example of the compound (3) includes long-chain alcohols having a linear or branched alkyl group or alkenyl group and a mixture thereof; preferably includes long-chain alcohols having a linear or branched alkyl group or alkenyl group having 12–26 carbons; and further preferably includes long-chain alcohols such as cetanol, cetyl alcohol, stearyl alcohol, icosanol, behenyl alcohol, tetracosanol and ceryl alcohol. More preferred ones are tetradecyl alcohol, cetyl alcohol, cetanol, stearyl alcohol and a mixture thereof, and cetyl alcohol is particularly preferred. In cetanol of the present invention, cetyl alcohol is a main component and higher alcohols such as stearyl alcohol and oleyl alcohol are comprised therein.

With regard to the molar ratio of the compounds (1) to (2) in the quaternization, (1):(2)=1:1–1:1.5 is preferably and more preferably 1:1.01–1:1.2. The ratio by weight of the sum of the compounds (1) and (2) to the compound (3), i.e. [(1)+(2)]:(3), is preferably 5:95–95:5, more preferably 20:80–90:10 and particularly preferably 40:60–80:20, and it is preferred to set so as to make the melting point of the reaction final product 100° C. or lower.

The compound (3) which is a reaction solvent may be added at the quaternizing stage, or in the preparation of the compound (1), may be used in such a manner that the starting alcohol is used excessively to the monohalogen-carboxylic acid and used as it is as a solvent for quaternization.

An example of the preparation of the compound (4) by the method of the present invention is that all amount of the compound (2) is added to a mixture of the compounds (1) and (3) under a high pressure of 0.1–1.0 MPa and made to react at the reaction temperature of 40–100° C. for 1–5 hours. Alternatively, the reaction may be carried out by adding the compound (2) gradually.

For the betaine alkyl ester mixture prepared as such, because the compound (3) used as a solvent is an oily component. Therefore, it is possible that the reaction final product may be used, as it is, without removal of the compound (3) to be compounded in a cosmetic and then to be emulsified for the gelatinous state. It is also possible that, if necessary, the mixture may be compounded after removal of an excessive amine. When a substance having a lower melting point is necessary for compounding, it is possible that, further, the melting point is lowered by adding propylene glycol or the like for example and then the product is used for the compounding.

Incidentally, the compound (4) may be separated from the betaine alkyl ester mixture of the present invention and used for various uses and, in that case, its purification may be simple or unnecessary when the compound (3) has no problem in view of safety and can reside differing from toluene whereby the compound (4) can be obtained efficiently and that is advantageous.

An oily substance such as long-chain alcohol and ester oil and/or a silicone may be used if necessary in the cosmetic for hair using the betaine alkyl ester mixture of the present invention.

With regard to the long-chain alcohol, those which are exemplified for the compound (3) may be used.

With regard to the ester oil, lower alcohol ester of fatty acids is exemplified and isopropyl palmitate is preferred.

With regard to the silicone, the following (A)–(K) may be cited for example.

(A) Dimethylpolysiloxane represented by the following formula (I)

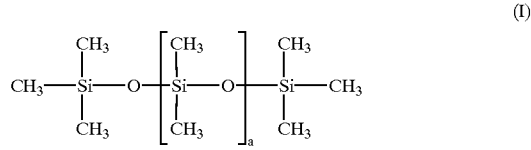

(I)

(wherein a shows 3–20000)
(B) Methylphenylpolysiloxane
(C) Amino-modified silicone Particularly preferred amino-modified silicone is that which is represented by the formula (II),

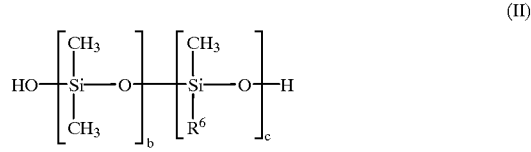

(II)

[wherein $R^6$ is an aminoalkyl group represented by the formula

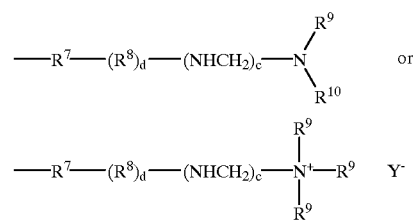

(wherein $R^7$ is a divalent hydrocarbon group; $R^8$ is —OCH$_2$CH$_2$—,

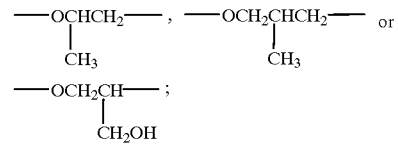

each of $R^9$ and $R^{10}$ is a hydrogen atom or a monovalent hydrocarbon group; each of d and e is an integer of 0–6; and $Y^-$ is a halogen ion or an organic anion); and each of b and c is an integer depending upon a molecular weight].

More preferred substance is that has $R^6$ being —(CH$_2$)$_3$—NH—(CH$_2$)$_2$—NH$_2$ and an average molecular weight being 3000–100000 [,that is Amodimethicone].

It is preferred that the above amino-modified silicone is used as an aqueous emulsion and the said aqueous emulsion may be obtained according to a method mentioned, for example, in JP-B 56-38609 that cyclic diorganopolysiloxane and organo dialkoxysilane are subjected to an emulsifying-polymerization in the presence of a surfactant of a quaternary ammonium salt type and water.

When the above amino-modified silicone is used as an aqueous emulsion, amount of the amino-modified silicone contained in the said aqueous emulsion is preferably 20–60% by weight and more preferably 30–50% by weight. Examples of the preferred aqueous emulsion of amino-modified silicone are SM 8704 C (provided by Toray Silicone Co. Ltd.) and DC 939 (provided by Dow Corning).

(D) Fatty acid-modified polysiloxane, (E) Alcohol-modified silicone, (F) Aliphatic alcohol-modified polysiloxane, (G) Polyether-modified silicone, (H) Epoxy-modified silicone, (I) Fluorine-modified silicone, (J) Cyclic silicone, (K) Alkyl-modified silicone.

In the case of a cosmetic for hair of a rinsing-out type such as a rinse and a conditioner, preferred silicones among the above are (A) [in the formula (I), a may be selected from 3–20000 depending upon the object of the finished feeling and, for a light finish type, 100–1000 is preferred], (C), (F), (G) and (J). In the case of a cosmetic for hair of a non-rinsing type such as a hair-cream, preferred silicones are (A) [with an object of a reduction in oily feeling, a in the formula (I) is preferably 2000–8000], (B), (C), (G) and (J).

Amount of the compound (4) in the cosmetic for hair of the present invention is preferably 0.1–20% by weight and, more preferably, 1–10% by weight. Amount of 0.1% by weight or more gives a good touch while that of 20% by weight or less results in no problem in terms of stability of the product during its storage such as precipitation, solidification, separation, etc.

Besides the above-mentioned components, the cosmetic for hair of the present invention may be compounded with a surf actant such as cationic surfactant other than the compound (4), anionic surfactant, nonionic surfactant and amphoteric surfactant, hydrocarbon, lanolin derivative, higher fatty acid, fat/oil, glycerol, moisturizer, cationic polymer, polysaccharide, polypeptide, pearling agent, solvent, base for forming liquid crystals, aromatic sulfonic acid, dye, perfume, propellant, chelating agent, pH adjusting agent, preservative and anti-dandruff agent unless the object of the present invention is deteriorated. These components may be compounded by combining two or more by taking the property of each component into consideration.

The cosmetic for hair of the present invention may be used for hair-rinse, hair-conditioner, hair-treatment, hair-pack, hair-cream, and the like.

EXAMPLES

Example 1

150.0 g of cetyl ester of monochloro acetic acid and 177.8 g of cetyl alcohol were charged in an autoclave, 33.4 g of trimethylamine were compressed thereinto and the reaction was carried out at 80° C. for 3 hours. After completion of the reaction, an excessive trimethylamine was evaporated under reduced pressure to give 354.4 g of glycine betaine cetyl ester mixture (hereinafter, referred to as "mixture 1"). The mixture 1 was analyzed by a liquid chromatography whereupon the composition of the mixture 1 was found to be 50% by weight of glycine betaine cetyl ester and 50% by weight of cetyl alcohol. Compositions of the mixtures in the following Examples and Comparative Examples were determined by the same manner.

Example 2

150.0 g of cetyl ester of monochloroacetic acid and 569.5 g of cetanol (Kalcohl 6870; provided by Kao Corporation) were charged in an autoclave, 41.3 g of dimethylethylamine were compressed thereinto and the reaction was carried out at 60° C. for five hours. After completion of the reaction, an excessive dimethylethylamine was evaporated under reduced pressure to give 732.4 g of glycine betaine cetyl ester mixture (hereinafter, referred to as "mixture 2"). Composition of the mixture 2 was 20% by weight of glycine betaine cetyl ester and 80% by weight of cetanol.

Example 3

215 g of a reaction product (which comprises 65 g of tetradecyl alcohol and 150.0 g of monochloroacetic acid tetradecyl ester) resulted by reaction of used excessive tetradecyl alcohol was charged in an autoclave, 33.4 g of trimethylamine was compressed thereinto and the reaction was carried out at 80° C. for 3 hours. After completion of the reaction, an excessive trimethylamine was evaporated under reduced pressure to give 236.2 g of glycine betaine tetradecyl ester mixture (hereinafter, referred to as "mixture 3"). Composition of the mixture 3 was 71% by weight of glycine betaine tetradecyl ester and 29% by weight of tetradecyl alcohol.

Comparative Example 1

The same operation as in Example 1 was carried out except that 177.8 g of ethanol was used instead of cetyl alcohol and that the reaction was carried out at 50° C. to give a glycine betaine cetyl ester mixture (hereinafter, referred to as "comparative mixture 1"). Charging was done in such a manner that the composition of the comparative mixture 1 was made 50% by weight of glycine betaine cetyl ester and 50% by weight of ethanol but, due to a transesterification by ethanol, the amount of glycine betaine cetyl ester did not reach 30% by weight.

Comparative Example 2

The same operation as in Example 2 was carried out except that 79.0 g of ethanol was used instead of cetanol and the reaction was carried out at 50° C. to give glycine betaine cetyl ester mixture (hereinafter, referred to as "comparative mixture 2"). Charging was done in such a manner that the composition of the comparative mixture 2 was made 71% by weight of glycine betaine cetyl ester and 29% by weight of ethanol but, due to a transesterification by ethanol, the amount of glycine betaine cetyl ester did not reach 50% by weight. Examples 4 and 5 and Comparative Examples 3 and 4

[Evaluation of Properties]

According to the compositions as shown in Table 1, hair-rinse agents of Examples 4–6 and Comparative Examples 3–4 comprising the mixtures 1–3 and the comparative mixtures 1–2 were prepared by a conventional method. These hair-rinse agents were subjected to an observation for the emulsified state by naked eye and, in addition, softness, etc. were evaluated by an organoleptic means by the following method. The result is shown in Table 1.

<Method of Evaluation>

20 g of hair (length of 20 cm, average diameter of 60μm) of a Japanese lady, which was not subjected to a chemical treatment such as cold permanent-wave, was tied and washed with 5 g of shampoo. Composition of this shampoo was 15% by weight of polyoxyethylene alkyl (having 12 carbons) ether sulfate (average added molar numbers of ethylene oxide of 2.5) sodium salt, 3% by weight of diethanolamide and water in balance. After that, 2.0 g of the hair rinse prepared as above were uniformly applied and rinsed with running water of 40° C. for 30 seconds. Softness, smoothness and oily feeling of the hair upon rinsing were evaluated according to the following criteria.

⊚: very good, ○: good, X: poor

TABLE 1

|  | Examples | | | Comparative example | |
|---|---|---|---|---|---|
|  | 4 | 5 | 6 | 3 | 4 |
| Compounded component (% by weight) | | | | | |
| Mixture 1 | 2 | | | | |
| Mixture 2 | | 5 | | | |
| Mixture 3 | | | 1.4 | | |
| Comparative mixture 1 | | | | 2 | |
| Comparative mixture 2 | | | | | 1.4 |
| cetanol | 3 | | 3.6 | 4 | 4 |
| Deionized water adjusted to pH 3.5 with citric acid | 95 | 95 | 95 | 94 | 94.6 |
| Content of glycine betaine alkyl ester | 1 | 1 | 1 | 1*1 | 1*1 |
| Content of long-chain alcohol | 4 | 4 | 4 | 4 | 4 |
| Emulsifying property | Emulsified into a gelatinous form | Emulsified into a gelatinous form | Emulsified into a gelatinous form | Emulsified into a gelatinous form | Emulsified into a gelatinous form |
| Softness | ⊚ | ⊚ | ⊚ | X | X |
| Smoothness | ⊚ | ⊚ | ⊚ | X | X |
| Oily feeling | ⊚ | ⊚ | ○ | X | X |

*1: Charged in such an amount to make 1% by weight but the content did not reach 1% by weight

Example 7

(Hair-rinse Agent)

A hair-rinse having the following composition was prepared.

| Mixture 2 | 5.0% by weight |
| Isopropyl palmitate | 0.5% by weight |
| Dimethylpolysiloxane (average molecular weight = 9000) | 1.5% by weight |
| Polyether-modified silicone | 0.5% by weight |
| Propylene glycol | 2.0% by weight |
| 50% aqueous solution of citric acid | 0.06% by weight |
| Perfume, methylparaben | Proper quantity |
| Pure water | Balance |

This rinse was emulsified in gelatinous state and softness, smoothness and oily feeling upon rinsing were very good.

Example 8

(Hair-treatment)

A hair-treatment having the following composition was prepared.

| Mixture 1 | 15.0% by weight |
| Cetanol | 1.0% by weight |
| Dimethylpolysiloxane (average molecular weight = 9000) | 5.0% by weight |
| Monostearic acid polyoxyethylene sorbitan (average added molar numbers of ethylene oxide = 20) | 0.5% by weight |
| Behenic acid | 1.0% by weight |
| Dipropylene glycol | 6.0% by weight |
| Glycerol | 10.0% by weight |
| 50% Aqueous solution of citric acid | 0.6% by weight |
| Perfume and methyl paraben | proper quantity |
| Pure water | balance |

This hair-treatment was emulsified in gelatinous state and flexibility, smoothness and oily feeling upon rinsing were very good.

What is claimed is:

1. A method for preparing a betaine alkyl ester mixture, which comprises reacting a monohalogen-carboxylic acid alkyl-ester represented by the following formula (1):

$$R^1-O-CO-R^2-X \qquad (1)$$

wherein $R^1$ is a linear or branched alkyl group or alkenyl group having 8–40 carbon atoms; $R^2$ is a linear or branched alkylene group having 1–5 carbon atoms; and X is a halogen atom;

with a tertiary amine represented by the following formula (2):

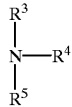

$$(2)$$

wherein $R^3$, $R^4$ and $R^5$ are same as or different from each other and each of them is a linear or branched alkyl group, alkenyl group or hydroxyalkyl group having 1–24 carbon atoms, using a long-chain alcohol represented by following formula (3) as a reaction solvent:

$$R-OH \qquad (3)$$

wherein R is a linear or branched alkyl group or alkenyl group having 8–40 carbon atoms on average;

to prepare the betaine alkyl ester mixture comprising a betaine alkyl ester represented by the following formula (4):
(4)
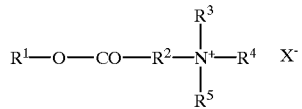
wherein $R^1$, $R^2$, $R^3$, $R^4$, $R^5$ and X have the same meanings as defined above,
and the long-chain alcohol represented by the above-mentioned formula (3).
* * * * *